(12) United States Patent
Kubo et al.

(10) Patent No.: US 8,439,823 B2
(45) Date of Patent: May 14, 2013

(54) ENDOSCOPE APPARATUS AND ITS CONTROL METHOD

(75) Inventors: Masahiro Kubo, Tokyo (JP); Makoto Kagaya, Tokyo (JP); Masayuki Takahira, Tokyo (JP); Masayuki Kuramoto, Tokyo (JP); Shuichi Ishii, Tokyo (JP); Ryo Takahashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 690 days.

(21) Appl. No.: 12/622,818

(22) Filed: Nov. 20, 2009

(65) Prior Publication Data
US 2010/0130819 A1    May 27, 2010

(30) Foreign Application Priority Data
Nov. 21, 2008    (JP) .................................. 2008-297601

(51) Int. Cl.
*A61B 1/04*    (2006.01)
(52) U.S. Cl.
USPC ........................................................ 600/109
(58) Field of Classification Search ................... 600/109
See application file for complete search history.

(56) References Cited

U.S. PATENT DOCUMENTS

| 5,209,220 | A | * | 5/1993 | Hiyama et al. ............... 600/109 |
| 5,784,098 | A | * | 7/1998 | Shoji et al. ...................... 348/45 |
| 6,582,362 | B2 | | 6/2003 | Konno | |
| 7,828,721 | B2 | * | 11/2010 | Kumei et al. ................. 600/109 |
| 2002/0055669 | A1 | | 5/2002 | Konno | |
| 2010/0049058 | A1 | * | 2/2010 | Ishihara ....................... 600/477 |

FOREIGN PATENT DOCUMENTS

| EP | 1 905 347 | 4/2008 |
| JP | 4-013112 A | 1/1992 |
| JP | 9-026547 A | 1/1997 |
| JP | 2002-253488 A | 9/2002 |
| JP | 2003-93336 A | 4/2003 |
| JP | 2005-026875 A | 1/2005 |
| JP | 2007-20728 A | 2/2007 |
| WO | WO 2008/078742 | 7/2008 |

\* cited by examiner

*Primary Examiner* — Rodney Fuller
(74) *Attorney, Agent, or Firm* — Birch, Stewart, Kolasch & Birch, LLP

(57) ABSTRACT

An imaging mode is automatically switched based on the kind of a subject. The spatial frequency of an endoscopic image obtained by imaging the subject is detected. Further, judgment is made, based on the distribution of the spatial frequency, as to whether the endoscopic image was obtained by performing close-up imaging on the subject. The condition of imaging is switched based on the result of judgment as to whether the image was obtained by close-up imaging or distant-view imaging.

6 Claims, 4 Drawing Sheets

| PARAMETER (WAVELENGTH) | $M_{j0}$ | $M_{j1}$ | $M_{j2}$ |
|---|---|---|---|
| p1 | 0.000083 | −0.00188 | 0.003592 |
| ⋮ | ⋮ | ⋮ | ⋮ |
| p18 | −0.00115 | 0.000569 | 0.003325 |
| p19 | −0.00118 | 0.001149 | 0.002771 |
| p20 | −0.00118 | 0.001731 | 0.0022 |
| p21 | −0.00119 | 0.002346 | 0.0016 |
| p22 | −0.00119 | 0.00298 | 0.000983 |
| p23 | −0.00119 | 0.003633 | 0.000352 |
| ⋮ | ⋮ | ⋮ | ⋮ |
| p43 | 0.003236 | 0.001377 | −0.00159 |
| p44 | 0.003656 | 0.000671 | −0.00126 |
| p45 | 0.004022 | 0.000068 | −0.00097 |
| p46 | 0.004342 | −0.00046 | −0.00073 |
| p47 | 0.00459 | −0.00088 | −0.00051 |
| p48 | 0.004779 | −0.00121 | −0.00034 |
| p49 | 0.004922 | −0.00148 | −0.00018 |
| p50 | 0.005048 | −0.00172 | −0.000036 |
| p51 | 0.005152 | −0.00192 | 0.000088 |
| p52 | 0.005215 | −0.00207 | 0.000217 |
| ⋮ | ⋮ | ⋮ | ⋮ |
| p61 | 0.00548 | −0.00229 | 0.00453 |

DB

CLOSE-UP ENLARGEMENT MODE

DISTANT-VIEW MODE

ENDOSCOPE APPARATUS AND ITS CONTROL METHOD

BACKGROUND OF THE INVENTION

1. Field of the Invention

The present invention relates to an endoscope apparatus that controls various imaging modes thereof and its control method.

2. Description of the Related Art

An endoscope apparatus is used to diagnose the condition of the body cavity of a patient, such as the esophagus, stomach and large intestine, by using images (image diagnosis, which is diagnosis by observing images of the body cavity of the patient or the like). The endoscope apparatus obtains images of the body cavity of the patient by a scope inserted into the body cavity. In recent years, when diagnosis is performed by using images obtained by the endoscope, endoscopic images obtained by the scope of the endoscope are displayed on a monitor in real time. A doctor performs image diagnosis while looking at the monitor. Therefore, the doctor can diagnose the patient while recognizing the positions of the images displayed on the monitor. Meanwhile, observation modes using endoscopes include an ordinary observation mode, a fluorescent observation mode, and a narrow-band mode to help doctors easily perform image diagnosis. The ordinary observation mode observes a subject when white light is output to the subject. The fluorescent observation mode observes fluorescence output from the subject when the subject is illuminated with fluorescence. The narrow-band mode observes the subject when the subject is illuminated with narrow-band light.

Automatic switching of the various observation modes has been proposed so that doctors can perform efficient image diagnosis (for example, please refer to Japanese Unexamined Patent Publication No. 2007-020728 (Patent Literature 1)). Patent Literature 1 proposes automatically switching imaging modes among the ordinary observation mode, the narrow-band observation mode, and the fluorescent observation mode based on the magnification of a lens.

Further, automatic switching of the magnification of an imaging lens attached to the leading end of a scope based on the various imaging modes has been proposed (for example, please refer to U.S. Pat. No. 6,582,362 (Patent Literature 2)). Patent Literature 2 utilizes the tendency that when AEC (automatic exposure control) for controlling the diaphragm (aperture stop) of a light source unit to maintain the lightness of the image at a constant level is performed, if a distance to an object (subject) changes, the state of the diaphragm changes. In Patent Literature 2, the distance to the object is recognized based on the state of the diaphragm, and judgment is made, based on the distance, as to whether close-up imaging or distant-view imaging has been performed. If it is judged that close-up imaging has been performed, the high-frequency component of the obtained image is enhanced. If it is judged that distant-view imaging has been performed, the low-frequency component of the obtained image is enhanced.

Besides the case proposed in Patent Literature 2, which measures the distance between the scope and the subject by using AEC, automatic switching of close-up imaging and distant-view imaging based on the region to be imaged is desired to perform efficient image diagnosis.

SUMMARY OF THE INVENTION

In view of the foregoing circumstances, it is an object of the present invention to provide an endoscope apparatus that can automatically switch the imaging mode based on the kind of a subject. Further, it is another object of the present invention to provide a control method of the endoscope apparatus.

An endoscope apparatus of the present invention is an endoscope apparatus comprising:

a scope that obtains an endoscopic image by imaging a subject;

a frequency analysis means that analyzes the spatial frequency of the endoscopic image obtained by the scope;

an imaging state judgment means that judges, based on the distribution of the spatial frequency analyzed by the frequency analysis means, whether the subject has been imaged by close-up imaging or by distant-view imaging; and a condition switching means that switches, based on the result of judgment by the imaging state judgment means as to whether the subject has been imaged by close-up imaging or by distant-view imaging, the condition of imaging the subject.

A control method of an endoscope apparatus of the present invention is a control method of the endoscope apparatus that obtains an endoscopic image by imaging a subject by using a scope, the method comprising the steps of:

analyzing the spatial frequency of the endoscopic image;

judging, based on the distribution of the analyzed spatial frequency, whether the subject has been imaged by close-up imaging or by distant-view imaging; and switching, based on the result of judgment as to whether the subject has been imaged by close-up imaging or by distant-view imaging, the condition of imaging the subject.

Here, the term "close-up imaging" means imaging performed in a state in which the subject and the leading end of the scope or a hood (cover) attached to the leading end of the scope are in contact with each other, or substantially in contact with each other (positions are extremely similar to the contact state). In contrast, the term "distant-view imaging" means imaging performed when the leading end of the scope and the subject are away from each other.

Further, the condition of imaging (imaging condition) should be switched to a condition that is appropriate for the close-up imaging or the distant-view imaging. The term "condition of imaging" refers to a known imaging condition, such as the magnification (magnification ratio) of imaging, the magnification of an electronic zoom, the amount of light output to the subject, and image processing condition, for example.

The imaging state judgment means should judge, based on the distribution of the spatial frequency analyzed by the frequency analysis means, whether the subject has been imaged by close-up imaging or by distant-view imaging. It is desirable that the imaging state judgment means judges that the subject has been imaged by close-up imaging when the distribution of the spatial frequency is on the high-frequency side, and that the imaging state judgment means judges that the subject has been imaged by distant-view imaging when the distribution of the spatial frequency is on the low-frequency side.

Further, the frequency analysis means may analyze the spatial frequency of an endoscopic image obtained by illuminating a subject with white light. Alternatively, the frequency analysis means may analyze the spatial frequency of a spectral image or images. In such a case, the endoscope apparatus further includes a spectral image generation means that generates a spectral estimation image or images by performing a matrix operation on the endoscopic image obtained by illuminating the subject with white light.

Further, in the endoscope apparatus of the present invention, the scope may include an imaging lens for changing the magnification of imaging. Further, the condition switching means may control the condition of imaging by controlling the magnification of the imaging lens. The condition switching means may increase the magnification of the imaging lens when it is judged that the subject has been imaged by close-up imaging. In contrast, when it is judged that the subject has been imaged by distant-view imaging, the condition switching means may decrease the magnification of the imaging lens.

Further, the scope may include a light illumination means that outputs light to the subject, and the condition switching means may control the condition of imaging by controlling the amount of light. When the mode of imaging is switched to close-up (enlargement) mode, the amount of light output from the light illumination means may be decreased. When the mode of imaging is switched to distant-view imaging mode, the amount of light output from the light illumination means may be increased.

According to the endoscope apparatus of the present invention and the control method of the endoscope apparatus, the endoscope apparatus obtains an endoscopic image by imaging a subject by using a scope. The control method of the endoscope apparatus includes the steps of:

analyzing the spatial frequency of the endoscopic image;

judging, based on the distribution of the analyzed spatial frequency, whether the subject has been imaged by close-up imaging or by distant-view imaging; and switching, based on the result of judgment as to whether the subject has been imaged by close-up imaging or by distant-view imaging, the condition of imaging the subject. Therefore, it is possible to estimate, based on an obtained endoscopic image, a subject (a region to be observed or the like) that an operator (observer, doctor or the like) wants to observe, and to switch the imaging mode to a mode that is appropriate for the region to be observed. Therefore, the operator does not need to switch the imaging mode. Hence, efficient image diagnosis is possible.

Further, the imaging state judgment means may judge that the subject has been imaged by close-up imaging when the distribution of the spatial frequency is on the high-frequency side. In contrast, when the distribution of the spatial frequency is on the low-frequency side, the imaging state judgment means may judge that the subject has been imaged by distant-view imaging. The imaging state judgment means judges in such a manner by utilizing the characteristic that in close-up imaging, images of densely-present fine blood vessels or capillaries, an uneven pattern on the surface of the subject (region), and the like are included in endoscopic images, and the spatial frequency components are distributed on the high-frequency side. Hence, it is possible to accurately judge whether close-up imaging has been performed.

The endoscope apparatus may further include a spectral image generation means that generates a spectral estimation image by performing a matrix operation on the endoscopic image obtained by illuminating the subject with white light. Further, the frequency analysis means may analyze the spatial frequency by using the spectral estimation image generated by the spectral image generation means. In such a case, it is possible to accurately judge whether close-up imaging or distant-view imaging has been performed.

Further, the scope may include an imaging lens for changing the magnification of imaging. Further, the condition switching means may increase the magnification of the imaging lens when it is judged that the subject has been imaged by close-up imaging. The condition switching means may decrease the magnification of the imaging lens when it is judged that the subject has been imaged by distant-view imaging. In such a case, it is possible to automatically set the magnification of imaging that is appropriate for each of close-up imaging and distant-view imaging. Hence, efficient image diagnosis is possible.

The scope may include a light illumination means that outputs light to the subject. Further, the condition switching means may decrease the amount of light output from the light illumination means when the mode has been switched to the close-up enlargement mode. The condition switching means may increase the amount of light output from the light illumination means when the mode has been switched to distant-view imaging mode. In such a case, it is possible to automatically set the amount of light that is appropriate for each of the close-up imaging and the distant-view imaging. Hence, efficient image diagnosis is possible.

DESCRIPTION OF THE PREFERRED EMBODIMENTS

Figure 1:
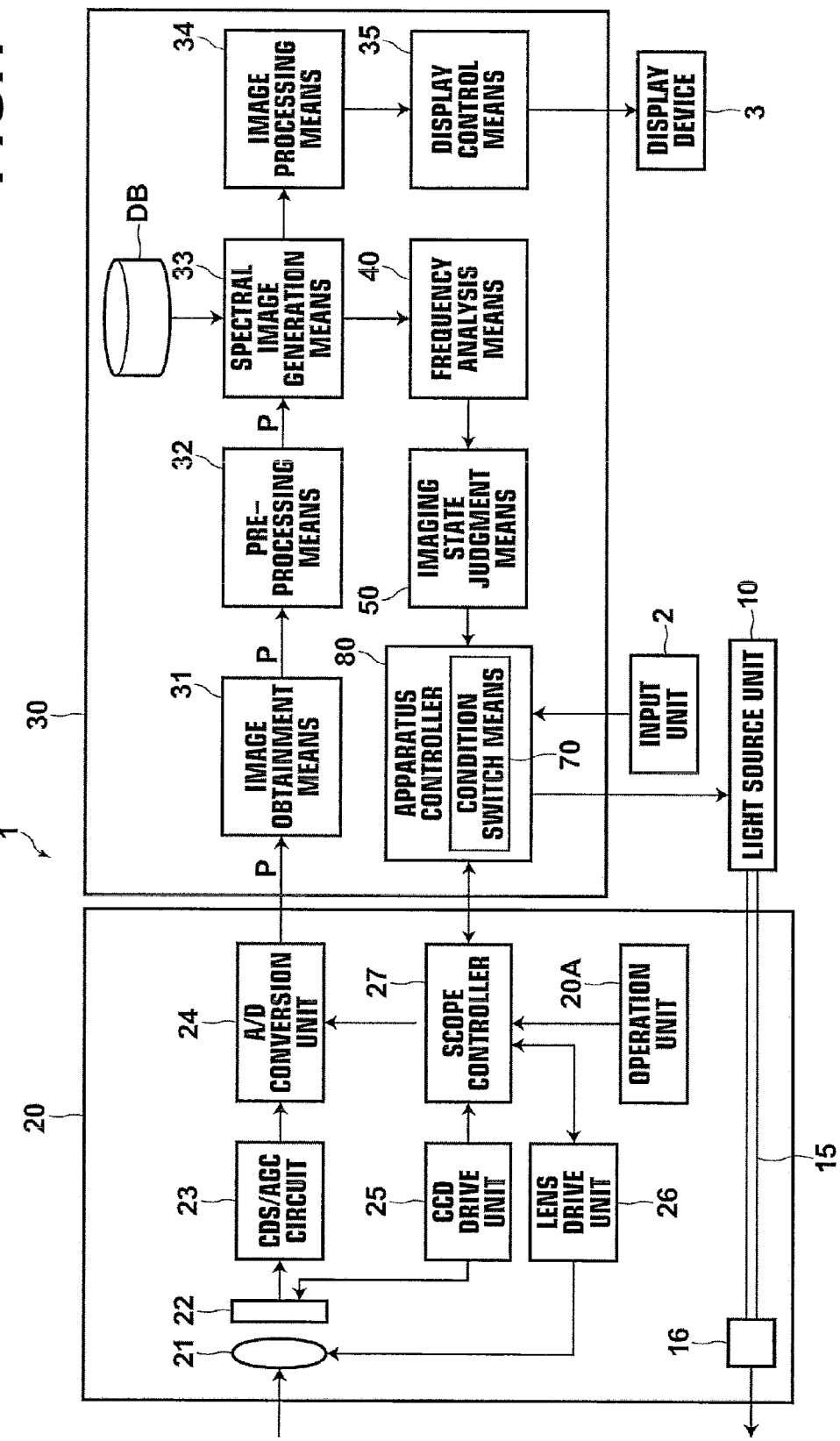
FIG. 1 is a block diagram illustrating an embodiment of an endoscope apparatus according to the present invention.

Hereinafter, embodiments of the present invention will be described with reference to drawings. FIG. 1 is a block diagram illustrating an example of an endoscope apparatus according to the present invention. An endoscope apparatus 1 includes a light source unit 10, a scope 20, and an image processing apparatus 30. The light source 10 outputs light to a subject so as to observe the subject by using an endoscope. The light source unit 10, such as a xenon lamp, outputs white light for performing ordinary observation. The light source unit 10 is optically connected to a light guide 15 of the scope 20. White light L1 output from the light source 10 enters the light guide 15, and is output from an observation window 16 to the subject. The amount of light output from the observation window 16 is controlled by an apparatus controller 80.

The scope 20 includes an imaging lens 21, an imaging device 22, a CDS/AGC (correlated double sampling/automatic gain control) circuit 23, an A/D (analog to digital) converter 24, a CCD (charge coupled device) drive unit 25, a lens drive unit 26, and the like. Further, each of these units is controlled by a scope controller 27. For example, the imaging lens 21 includes a set of a plurality of lenses, and the magnification of imaging is changed by being driven by the lens drive unit 26. The imaging device 22 includes a CCD, a CMOS (complementary metal oxide semiconductor) or the like. The imaging device 22 obtains an image by performing photoelectric conversion on an image of a subject imaged by the imaging lens 21. As the imaging device 22, a complementary-color type device or a primary-color type device may be used for example. The complementary-color type device has a color filter of Mg (magenta), Ye (yellow), Cy (cyan), and G (green) on the imaging surface. The primary-color type device has a color filter of RGB on the imaging surface. Further, the operation of the imaging device 22 is controlled by the CCD drive unit 25. When the imaging device 22 has obtained an image (video) signal, the CDS/AGC (correlated double sampling/automatic gain control) circuit 23 performs sampling on the obtained signal, and amplifies the sampled signal. Further, the A/D converter 24 performs A/D conversion on an endoscopic image output from the CDS/AGC circuit 23, and outputs a digital signal to the image processing apparatus 30.

The image processing apparatus 30 processes endoscopic images obtained by the scope 20. The image processing apparatus 30 is structured, for example, by DSP (digital signal processing) or the like. The image processing apparatus 30 includes an image obtainment means 31, a pre-processing means 32, an image processing means 34, and a display control means 35. The image obtainment means 31 obtains endoscopic image P obtained by imaging by the imaging device 22 of the scope 20. The pre-processing means 32 performs pre-processing on the endoscopic image P obtained by the image obtainment means 31. For example, the pre-processing means 32 has a function of converting signals represented in a YCC color system to signals represented in an RGB color system when the endoscopic image P is represented by YCC color system. Further, the pre-processing means 32 has a gamma conversion function, a gradation adjustment function, and the like.

The spectral image generation means 33 generates spectral estimation image SP by performing matrix operation on the endoscopic image P by using matrix parameter M. An example of the operation by the spectral image generation means 33 is described, in detail, in Japanese Unexamined Patent Publication No. 2003-093336.

Specifically, the spectral image generation means 33 generates the spectral estimation image SP by performing matrix operation represented by the following equation (1):

$$\begin{pmatrix} SP_r \\ SP_g \\ SP_b \end{pmatrix} = \begin{pmatrix} M_{00} & M_{01} & M_{02} \\ M_{10} & M_{11} & M_{12} \\ M_{20} & M_{21} & M_{22} \end{pmatrix} \cdot \begin{pmatrix} Pr \\ Pg \\ Pb \end{pmatrix}. \quad (1)$$

In the equation (1), $SP_r$, $SP_g$, and $SP_b$ represent RGB components of the spectral estimation image SP, respectively. Pr, Pg, and Pb represent RGB components of the endoscopic image P, respectively. A matrix of 3×3 including $M_{00}$ to $M_{22}$ represents matrix parameters M for performing the matrix operation.

Figure 2:
FIG. 2 is a table showing an example of matrix parameters used by a spectral image generation means illustrated in FIG. 1.

For example, as illustrated in FIG. 2, database DB stores matrix parameters $pi=(M_{j0}, M_{j1}, M_{j2})$ (i=1 to 61, j is the row of the matrix parameter M, and j=0 to 2). In the example illustrated in FIG. 2, the wavelength range of from 400 nm to 700 nm is divided into wavelength bands of 5 nm, and the matrix parameter is stored for each wavelength band of 5 nm. For example, when 500 nm, 620 nm, and 650 nm are selected as wavelength bands λ1, λ2, λ3, which constitute the spectral estimation image SP, the matrix operation is performed by using, as coefficients $(M_{j0}, M_{j1}, M_{j2})$, coefficients of the three parameters selected from 61 parameters in the table shown in FIG. 2. Specifically, coefficients (−0.00119, 0.002346, 0.0016) of parameter p21, which corresponds to the center wavelength of 500 nm, coefficients (0.004022, 0.000068, −0.00097) of parameter p45, which corresponds to the center wavelength of 620 nm, and coefficients (0.005152, −0.00192, 0.000088) of parameter p51, which corresponds to the center wavelength of 650 μm, are used to perform the matrix operation.

The combination of the parameters as described above is stored in the database DB for each region to be observed, such as blood vessels and tissue of a living body. The spectral estimation image SP is generated by using parameters that match each region of the body. For example, eight wavelength sets for setting the matrix parameters M are stored in the database DB. The eight wavelength sets are, for example, standard set CH1, blood-vessel sets CH2, CH3 for drawing blood vessels, tissue sets CH4, CH5 for drawing specific tissue, hemoglobin set CH6 for drawing a difference between oxyhemoglobin and deoxyhemoglobin, blood-carotene set CH7 for drawing a difference between blood and carotene, and blood-cytoplasm set CH8 for drawing a difference between blood and cytoplasm. The standard set CH1 is, for example, (λ1, λ2, λ3)=(400, 500, 600). The blood-vessel sets CH2, CH3 are, for example, (λ1, λ2, λ3)=(470, 500, 670) and (λ1, λ2, λ3)=(475, 510, 685), respectively. The tissue sets CH4, CH5 are, for example, (λ1, λ2, λ3)=(440, 480, 520) and (λ1, λ2, λ3)=(480, 510, 580), respectively. The hemoglobin set CH6 is, for example, (λ1, λ2, λ3)=(400, 430, 475). The blood-carotene set CH7 is, for example, (λ1, λ2, λ3)=(415, 450, 500). The blood-cytoplasm set CH8 is, for example, (λ1, λ2, λ3)=(420, 550, 600).

Particularly, the spectral image generation means 33 has a function of generating spectral estimation image SP for judging whether an image was obtained by close-up imaging or by distant-view imaging. For example, the spectral image generation means 33 generates a spectral estimation image of the wavelength of 415 nm and a spectral estimation image of the wavelength of 540 nm. When the wavelength of light is 415 nm, the depth of penetration of light is shallow, and when the wavelength of light is 540 nm, the depth of penetration of light is relatively deep.

The image processing means 34 illustrated in FIG. 1 performs enhancement processing or the like on the endoscopic image P and the spectral estimation images SP. The display control means 35 has a function of displaying the endoscopic image P that has been processed by the image processing means 34 on the display device 3 together with character information or the like.

Further, the image processing apparatus 30 includes a frequency analysis means 40, an imaging state judgment means 50, and a condition switching means 70. The frequency analysis means 40 performs frequency analysis on the spectral estimation images SP (wavelengths of 415 nm and 540 nm), generated by the spectral image generation means 33, to detect the spatial frequency components of the spectral estimation images SP. Here, a case in which the frequency analysis means 40 analyzes the spatial frequency components of the spectral estimation images SP is used as an example. However, it is not necessary that the frequency analysis is performed in such a manner. Alternatively, frequency analysis may be performed on an endoscopic image (ordinary observation image) P obtained when white light was output to the subject.

The imaging state judgment means 50 judges whether the endoscopic image P was obtained by close-up imaging or distant-view imaging. The imaging state judgment means 50 judges based on the spatial frequency components of the spectral estimation images SP analyzed by the frequency analysis means 40. The term "close-up imaging" means imaging performed in a state in which the subject and the leading end of the scope 20 or a hood (cover) attached to the leading end of the scope 20 are in contact with each other, or only slightly away from each other (they are not in contact with each other, but away from each other only by a small distance). In contrast, the term "distant-view imaging" means imaging performed when the leading end of the scope and the subject are away from each other.

Figure 3:
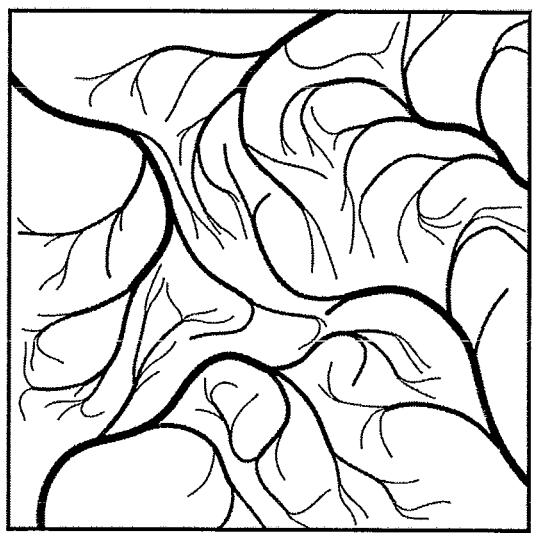
FIG. 3 is a schematic diagram illustrating an example of an endoscopic image obtained, by close-up imaging, by the endoscope apparatus illustrated in FIG. 1.
Figure 4:
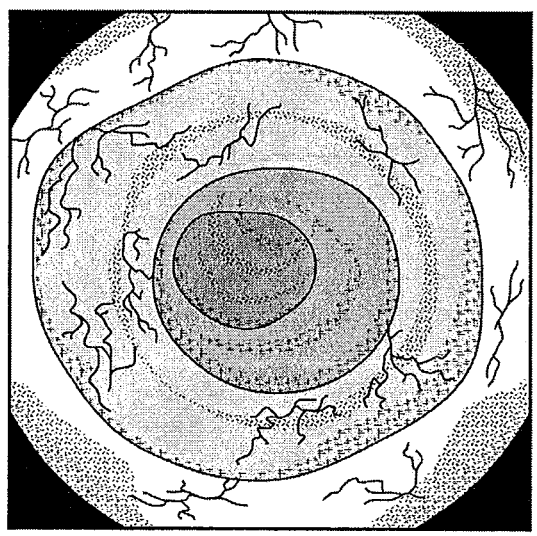
FIG. 4 is a schematic diagram illustrating an example of an endoscopic image obtained, by distant-view imaging, by the endoscope apparatus illustrated in FIG. 1.

Generally, close-up imaging is performed to obtain an image of a local region of the subject. Therefore, as illustrated in FIG. 3, an endoscopic image P obtained by close-up imaging includes images of fine blood vessels or capillaries, a fine uneven pattern of living tissue, a pit pattern or the like. Therefore, the frequency component of the endoscopic image P obtained by close-up imaging tends to be high. In contrast, an endoscopic image P obtained by positioning the leading end of the scope 20 away from the subject includes thick blood vessels, blood capillaries, the border or outline of living tissue, or the like, as illustrated in FIG. 4. Therefore, the frequency component of the endoscopic image P obtained by distant-view imaging is lower than that of the endoscopic image P obtained by close-up imaging.

Figure 5:
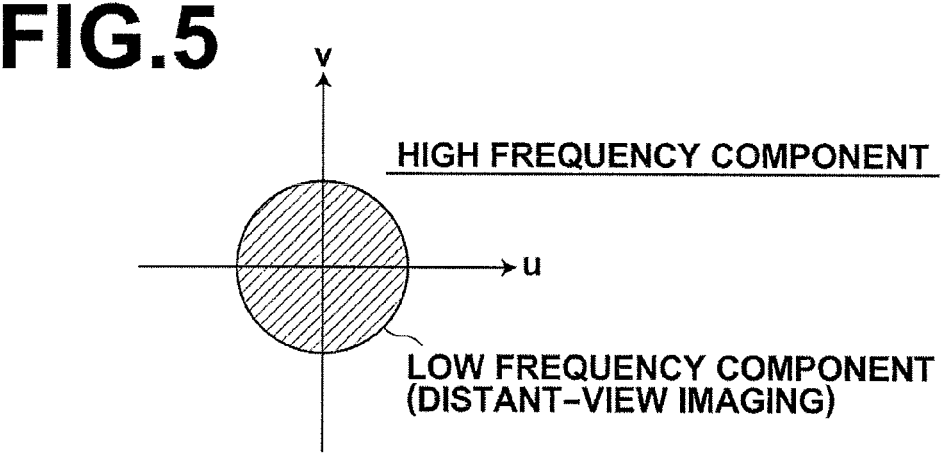
FIG. 5 is an example of the distribution of spatial frequency components analyzed by a frequency analysis means illustrated in FIG. 1.

Therefore, the imaging state judgment means 50 judges, for example, as illustrated in FIG. 5. Specifically, in Fourier space F (u, v), when the frequency component of an endoscopic image includes high-frequency component greater than a set threshold value, the imaging state judgment means 50 judges that the endoscopic image was obtained by close-up imaging. When the frequency component of an endoscopic image includes low-frequency component greater than a set threshold value, the imaging state judgment means 50 judges that the endoscopic image was obtained by distant-view imaging. When a plurality of spectral estimation images SP are used, the imaging state judgment means 50 may judge that the endoscopic image was obtained by close-up imaging when all of the plurality of spectral estimation images SP have been judged as spectral estimation images of close-up imaging. Alternatively, the imaging state judgment means 50 may judge that the endoscopic image was obtained by close-up imaging if at least one of the plurality of spectral estimation images SP has been judged as a spectral estimation image of close-up imaging. Accordingly, it is possible to estimate, based on the frequency component, a region that an operator (an operator of the endoscope) wants to observe. Further, it is possible to automatically switch the imaging mode to a mode that is most appropriate for the estimated region. Especially, when frequency analysis is performed on a plurality of spectral estimation images SP of different wavelengths, which have different depths of penetration of light, it is possible to accurately judge the imaging state.

The condition switching means 70 illustrated in FIG. 1 automatically switches the imaging condition based on the imaging state judged by the imaging state judgment means 50. Specifically, if the imaging state judgment means 50 judges that close-up imaging was performed, the condition switching means 70 increases the magnification of the imaging lens 21 of the scope 20 to a value higher than a standard value of magnification (for example, 20-power). The magnification of the imaging lens 21 is increased, for example, to 40 to 60-power, or higher. Further, the condition switching means 70 controls the light source unit 10 so that the amount of light output from the light illumination means 16 decreases. In contrast, if the imaging state judgment means 50 judges that distant-view imaging was performed, the condition switching means 70 reduces the magnification of the imaging lens 21 of the scope 20 to a value lower than a standard value of magnification (for example, to the same-size magnification (×1)). Further, the condition switching means 70 controls the light source unit 10 so that the amount of light output from the light illumination means 16 increases.

As described above, the imaging modes are automatically switched based on the frequency components of the endoscopic images P. Therefore, it is possible to automatically set the imaging condition that is appropriate for a region of the subject (patient) that the operator wants to observe. Unlike the conventional method, the operator does not need to set the magnification of imaging. Hence, efficient observation of the subject by using the endoscope is possible. A burden on the operator is reduced while efficient observation by using the endoscope is performed.

Figure 6:
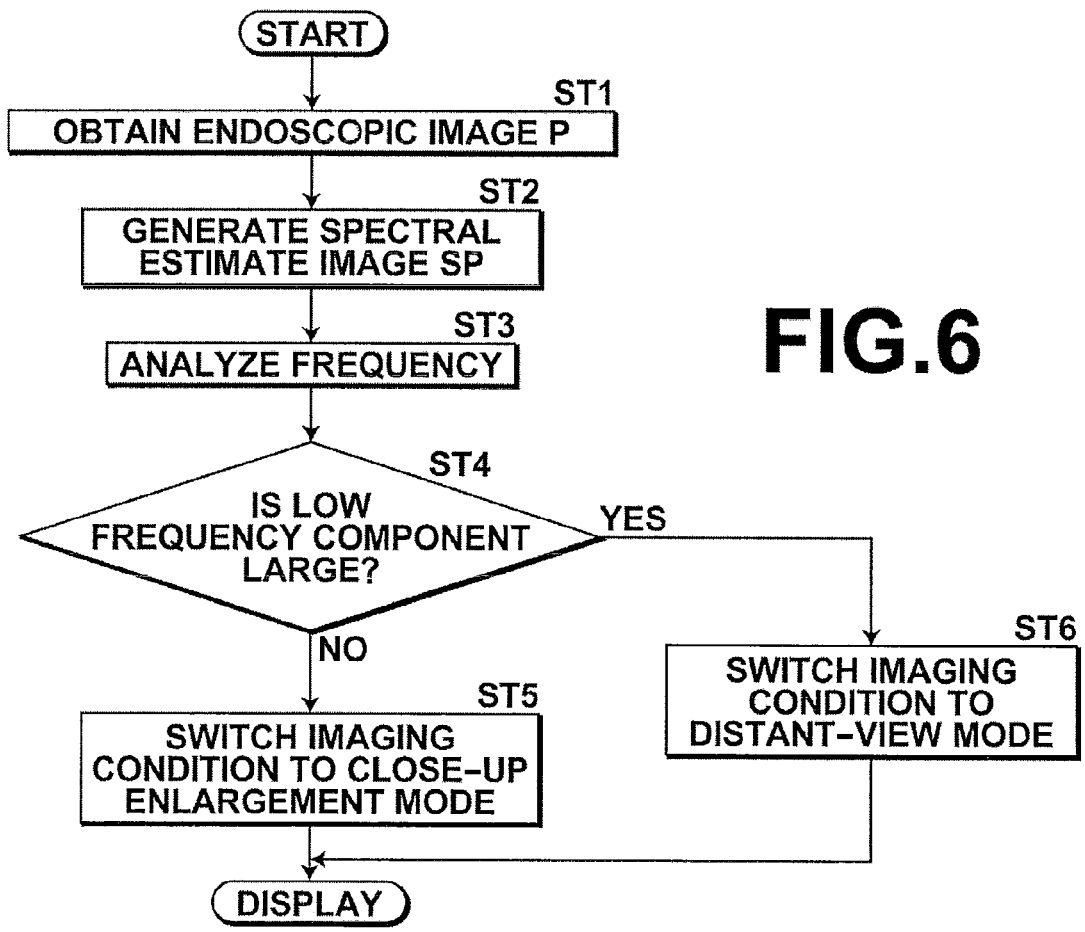
FIG. 6 is a flow chart illustrating an embodiment of a control method of the endoscope apparatus of the present invention.

FIG. 6 is a flow chart illustrating an embodiment of a control method of an endoscope apparatus of the present invention. With reference to FIGS. 1 through 6, the control method of the endoscope apparatus will be described. First, imaging is performed while the scope 20 is inserted into the body cavity of a patient. Accordingly, an endoscopic image P is obtained (step ST1). Then, the spectral image generation means 33 performs matrix operation, and generates a plurality of spectral estimation images SP of wavelengths of 415 nm and 540 nm (step ST2). After then, the frequency analysis means 40 detects and analyzes frequency components in each of the plurality of spectral estimation images SP. Further, the imaging state judgement means 50 judges whether the frequency component of each of the plurality of spectral estimation images SP is greater than or equal to a set threshold value (steps ST3 and ST4, please refer to FIG. 5).

When the distribution of the frequency components is on the high-frequency side, the condition switching means 70 sets the imaging mode to close-up enlargement mode (close-up mode). Further, the apparatus controller 80 sets the magnification of the imaging lens 21 to 30 to 60-power or the like, and the amount of light output from the light source unit 10 is reduced (step ST5). In contrast, when the distribution of the frequency components is on the low-frequency side, the condition switching means 70 sets the imaging mode to distant-view mode. Further, the apparatus controller 80 sets the magnification of the imaging lens 21 to the same-size magnification (×1) or the like, and the amount of light output from the light source unit 10 is increased (step ST6).

According to the aforementioned embodiment, when an endoscopic image P (SP) is obtained by imaging a subject by using a scope 20, the spatial frequency of the endoscopic image P is detected, and judgment is made, based on the distribution of the detected spatial frequency, as to whether the subject was imaged by close-up imaging or distant-view imaging. Further, the imaging condition is switched based on the result of judgment as to whether the subject was imaged by close-up imaging or by distant-view imaging. Therefore, it is possible to estimate, based on the endoscopic image, the subject that the operator wants to observe, and to switch the imaging mode to an imaging mode that is appropriate to observe the region to be observed. Hence, the operator does not need to switch the imaging mode, and efficient image diagnosis is possible.

When the distribution of the spatial frequency is on the high-frequency side, the imaging state judgment means 50 may judge that close-up imaging was performed. When the distribution of the spatial frequency is on the low-frequency side, the imaging state judgment means 50 may judge that distant-view imaging was performed. When the imaging state judgment means 50 makes judgment in such a manner, it is possible to utilize the characteristic that when an endoscopic image P is obtained by close-up imaging, the spatial frequency components tend to be on the high-frequency side, because the endoscopic image P includes dense fine blood-vessel images, an uneven pattern on the surface of the subject or the like. Hence, it is possible to accurately judge whether the endoscopic image was obtained by close-up imaging.

When the spectral image generation means 33 that generates spectral estimation image (images) SP by performing matrix operation on an endoscopic image P obtained by illuminating the subject with white light is further provided, and when the frequency analysis means analyzes the spatial frequency by using the spectral estimation image SP generated by the spectral image generation means 33, it is possible to accurately judge whether the endoscopic image was obtained by close-up imaging or by distant-view imaging.

Further, when the scope 20 includes the imaging lens 21 for changing the magnification of imaging, and when the condition switching means 70 increases the magnification of the imaging lens 21 if the endoscopic image was obtained by close-up imaging, and reduces the magnification of the imaging lens 21 if the endoscopic image was obtained by distant-view imaging, it is possible to automatically set the magnification to an appropriate value for each of close-up imaging and distant-view imaging. Hence, efficient image diagnosis is possible.

The scope 20 may include the light illumination means 16 that outputs light to the subject. Further, the condition switching means 70 may reduce the amount of light output from the light illumination means 16 when close-up imaging was performed. The condition switching means 70 may increase the amount of light output from the light illumination means 16 when the imaging operation has been switched to distant-view imaging. When the operation is performed in such a manner, it is possible to automatically set the amount of light that is appropriate for each of close-up imaging and distant-view imaging. Hence, efficient image diagnosis is possible.

The embodiments of the present invention are not limited to the aforementioned embodiments. For example, in the aforementioned embodiments, a case in which the condition switching means 70 switches, as the imaging condition, the magnification of imaging and the amount of light has been described. However, it is not necessary that the condition switching means 70 operates in such a manner. Alternatively, when close-up imaging was performed, the high-frequency component may be enhanced, and when distant-view imaging was performed, the low-frequency component may be enhanced. Alternatively, when close-up imaging was performed, the ratio of magnification of the electronic zoom may be increased, and when distant-view imaging was performed, the ratio of magnification of the electric zoom may be reduced. The image processing condition of the image processing means 34 may be switched in such a manner.

What is claimed is:

1. An endoscope apparatus comprising:
    a scope that obtains an endoscopic image by imaging a subject;
    a frequency analysis means that analyzes the spatial frequency of the endoscopic image obtained by the scope;
    an imaging state judgment means that judges, based on the distribution of the spatial frequency analyzed by the frequency analysis means, whether the subject has been imaged by close-up imaging or by distant-view imaging; and
    a condition switching means that switches, based on the result of judgment by the imaging state judgment means as to whether the subject has been imaged by close-up imaging or by distant-view imaging, the condition of imaging the subject.

2. An endoscope apparatus, as defined in claim 1, wherein the imaging state judgment means judges that the subject has been imaged by close-up imaging when the distribution of the spatial frequency is on the high-frequency side, and wherein the imaging state judgment means judges that the subject has been imaged by distant-view imaging when the distribution of the spatial frequency is on the low-frequency side.

3. An endoscope apparatus, as defined in claim 1, further comprising:
    a spectral image generation means that generates a spectral estimation image by performing a matrix operation on the endoscopic image obtained by illuminating the subject with white light, wherein the frequency analysis means analyzes the spatial frequency by using the spectral estimation image generated by the spectral image generation means.

4. An endoscope apparatus, as defined in claim 1, wherein the scope includes an imaging lens for changing the magnification of imaging, and wherein the condition switching means increases the magnification of the imaging lens when it is judged that the subject has been imaged by close-up imaging, and wherein the condition switching means decreases the magnification of the imaging lens when it is judged that the subject has been imaged by distant-view imaging.

5. An endoscope apparatus, as defined in claim 1, wherein the scope includes a light illumination means that outputs light to the subject, and wherein the condition switching means decreases the amount of the light output from the light illumination means when it is judged that the subject has been imaged by close-up imaging, and wherein the condition switching means increases the amount of the light output from the light illumination means when it is judged that the subject has been imaged by distant-view imaging.

6. A control method of an endoscope apparatus that obtains an endoscopic image by imaging a subject by using a scope, the method comprising the steps of:
    analyzing the spatial frequency of the endoscopic image;
    judging, based on the distribution of the analyzed spatial frequency, whether the subject has been imaged by close-up imaging or by distant-view imaging; and
    switching, based on the result of judgment as to whether the subject has been imaged by close-up imaging or by distant-view imaging, the condition of imaging the subject.

* * * * *